(12) United States Patent
Nix et al.

(10) Patent No.: US 9,498,875 B2
(45) Date of Patent: Nov. 22, 2016

(54) MULTI-PURPOSE TOOL

(71) Applicant: Wayne Douglas Nix, Youngsville, LA (US)

(72) Inventors: Wayne Douglas Nix, Youngsville, LA (US); Dawn Drury Nix, Youngsville, LA (US)

( * ) Notice: Subject to any disclaimer, the term of this patent is extended or adjusted under 35 U.S.C. 154(b) by 28 days.

(21) Appl. No.: 14/738,287

(22) Filed: Jun. 12, 2015

(65) Prior Publication Data

US 2015/0375385 A1 Dec. 31, 2015

Related U.S. Application Data

(60) Provisional application No. 62/016,830, filed on Jun. 25, 2014.

(51) Int. Cl.
 *F21V 33/00* (2006.01)
 *B25F 1/00* (2006.01)
 *B26B 13/22* (2006.01)

(52) U.S. Cl.
 CPC ............... *B25F 1/003* (2013.01); *B26B 13/22* (2013.01); *F21V 33/0084* (2013.01)

(58) Field of Classification Search
 CPC ...... B25F 1/003; B26B 1/005; B26B 11/008; B26B 13/22; F21V 33/0084
 See application file for complete search history.

(56) References Cited

U.S. PATENT DOCUMENTS

| | | | |
|---|---|---|---|
| 6,786,117 B1 * | 9/2004 | Tseng | B25B 7/00 81/303 |
| 2012/0195027 A1 * | 8/2012 | Russ | B26B 13/06 362/119 |
| 2014/0157524 A1 * | 6/2014 | Mote | B25F 1/003 7/156 |

* cited by examiner

*Primary Examiner* — Peggy Neils

(57) ABSTRACT

A multi-purpose tool operated by a user for storing, opening, cutting, clamping and holding of articles is provided. The multi-purpose tool includes a first shear, a second shear movably coupled to the first shear at a pivot point and a ratchet extending from each finger grip. Each shear includes a finger grip, cutting edges, tines and gripping tips. Further, the multi-purpose tool includes ratchet extending from respective finger grips. Each ratchet having a plurality of ratchet teeth defined therein, the ratchets extending towards each other. The first cutting edge and the second cutting edge are adapted for extending around the article in a firm grip by engagement of the ratchets in order to clamp the article between the first cutting edge and the second cutting edge.

9 Claims, 8 Drawing Sheets

MULTI-PURPOSE TOOL

CROSS REFERENCE TO RELATED APPLICATION

The present invention claims priority of the provisional patent application No. 62/016,830 filed on Jun. 25, 2014; all of which are incorporated herein by reference in their entireties.

BACKGROUND OF THE INVENTION

1. Field of the Invention

The present invention generally relates to a multi-functional scissor tool and more specifically, the present invention particularly relates to a multi-purpose tool operated by a user for storing, opening, cutting, clamping and holding of articles.

2. Description of Related Art

Multi-functional scissors are commonly used in day-to-day hospital and healthcare related activities to perform various procedures. Such procedures include cutting objects, opening lids of bottles, and shearing various materials including human tissue and textile material while performing surgery and other medical treatment. In existing multi-functional scissors, the scissor may include a variety of features such as a magnifying glass, a scaling function, or a cutting function having a simple structure and easy to use option with wide range of applications.

In other existing multi-functional scissor, the versatile cutting scissor can be used not only for shearing goods, but also to function as a screw tightener for repairing household appliances. In an existing multi-functional tool designed for the needs of healthcare professionals, the multi-functional tool may include individual tools that a healthcare professional uses on a regular basis that includes: a gas cylinder wrench, an integrated pill slicer, a sharp/dull neurological response tester, and a gripping device for intravenous caps.

Additional features may include a penlight or laser pointer and a fold out ruler. A tool carrier exists which includes features that healthcare professionals also regularly use, that include a tape roll holder and dispenser and retractable ring for keys and security badges. Various multi-purpose scissors available in the market fail to provide clamping of medical fluid tubes while holding the IV hub along with other features. Therefore, there is a need to provide a multi-purpose tool that allows clamping of medical tubing in between the gripping tips and further allowing holding of medical hubs which incrementally increases pressure in relation to the engagement of the ratchets.

Furthermore, there is a need to open the valve of gas cylinders, storage of tape, a plier/hemostat front metal grip allowing for opening and prying of various objects, and a metal teeth center allowing for gripping and opening bottles of medications and loosening IV pole screws.

SUMMARY OF THE INVENTION

In accordance with the teachings of the present invention, a multi-purpose tool operated by a user for storing, opening, cutting, clamping and holding of articles is provided.

An object of the present invention is to provide a multi-purpose tool including a first shear and a second shear movably coupled to the first shear at a pivot point. The first shear includes a first finger grip for receiving at least one finger of a user, a first tine extending from the first finger grip, a first cutting edge extending from the tine having a first curved inner surface front end, a first gripping tip attached to the front end of the first cutting edge.

The second shear includes a second finger grip for receiving at least one finger of a user, a second tine extending from the second finger grip positioned substantially parallel to the first tine, wherein the inner surface of the first tine and the second tine curved to form a first opening for holding articles when the first finger grip is in a closed position to the second finger grip.

The second shear further includes a second cutting edge extending from the second tine having a second curved inner surface front end, wherein the first curved inner surface front end and the second curved inner surface forms a second opening for holding substantially smaller articles when the first finger grip is in close position to the second finger grip, a second gripping tip attached to the second cutting edge for gripping of articles against the first gripping tip.

The multi-purpose tool further includes a ratchet extending from each finger grip, each ratchet having a plurality of ratchet teeth defined therein, the ratchets extend towards each other and wherein the first cutting edge and the second cutting edge are adapted for extending around the article in a firm grip by engagement of the ratchets in order to clamp the article between the first cutting edge inner surface front end or the first gripping tip and the second cutting edge inner surface front end or the second gripping tip front end.

Another object of the present invention is to provide a multi-purpose tool wherein the first opening stores at least one article such as medical tape, when the first finger grip is far from the second finger grip, further the article moves over at least one of the finger grips to store in the first opening.

Another object of the present invention is to provide a multi-purpose tool further includes a ruler bar either on the first shear or the second shear. Further, the multi-purpose tool includes an oxygen key attached to at least one of the finger grips, and a bottle opener configured in the inner surface of at least one the finger grips.

Further, the multi-purpose tool includes a screw driver tip configured on the outer surface of at least one of the finger grips. Further, the multi-purpose tool includes a light source protruding from the outer surface of at least one of the finger grips, and a power source configured in between at least one of the tine and at least one of the respective finger grips to power the light source.

Another object of the present invention is to provide the multi-purpose tool includes a carabineer configured in between at least one of the tines and at least one of the respective finger grips to secure articles.

These and other features and advantages will become apparent from the following detailed description of illustrative embodiments thereof, which is to be read in connection with the accompanying drawings.

Figure 1:
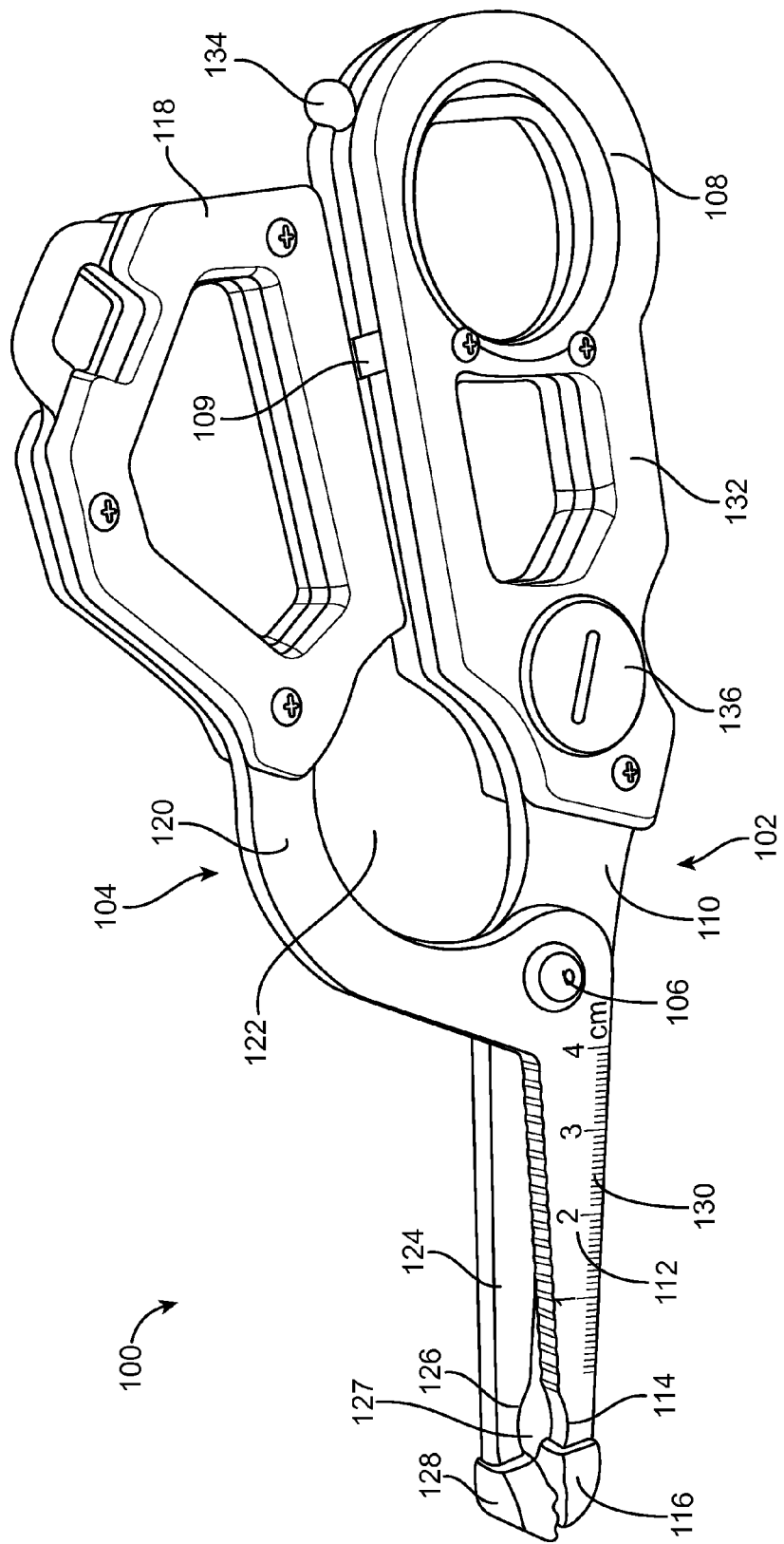
FIG. 1 illustrates a perspective view of a multi-purpose tool in accordance with a preferred embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

It will be appreciated that for simplicity and clarity of illustration, elements shown in the figures have not necessarily been drawn accurately or to scale. For example, the dimensions of some of the elements may be exaggerated relative to other elements for clarity. Similarly one or several physical components may be included in one functional block or element or divided into more than one functional unit or element.

DETAILED DESCRIPTION OF DRAWINGS

While this technology is illustrated and described in a preferred embodiment multi-purpose tool operated by a user for storing, opening, clamping, cutting and holding of articles to a user may be produced in many different configurations, forms and materials. There is depicted in the drawings, and will herein be described in detail, as a preferred embodiment of the invention, with the understanding that the present disclosure is to be considered as an exemplification of the principles of the invention and the associated functional specifications for its construction and is not intended to limit the invention to the embodiment illustrated. Those skilled in the art will envision many other possible variations within the scope of the technology described herein.

Reference will now be made in detail to several embodiments of the invention which are illustrated in the accompanying drawings. Wherever feasible and convenient, the same reference numerals are used in the figures and the description to refer to the same or like parts. The drawings are in a simplified form and not to precise scale. For purposes of convenience and clarity only, directional terms, such as top, bottom, left, right, up, down, over, above, below, beneath, rear, and front may be used with respect to the accompanying drawings.

These and similar directional terms should not be strictly construed to limit the scope of the invention. In addition, words such as attached, affixed, coupled, connected and similar terms with their inflectional morphemes are used interchangeably, unless the difference is noted or made otherwise clear from the context. These words and expressions do not necessarily signify direct connections, but include connections through mediate components and devices.

FIG. 1 illustrates a perspective view of a multi-purpose tool 100 for storing, cutting, clamping, opening and holding of articles (not shown in FIG. 1) in accordance with a preferred embodiment of the present invention. The multi-purpose tool 100 includes a first shear 102 and a second shear 104 movably coupled to the first shear at a pivot point 106. Examples of articles include but not limited to medical tape, bottle with cap, IV tubes, oxygen cylinder etc.

The first shear 102 includes a first finger grip 108 for receiving at least one finger of a user (not shown in FIG. 1), a first tine 110 extending from the first finger grip 108, a first cutting edge 112 extending from the first tine 110 is having a first curved inner surface front end 114, and a first gripping tip 116 attached to the first curved inner surface front end 114 of the first cutting edge 112.

The second shear 104 includes a second finger grip 118 for receiving at least one finger of the user and a second tine 120 extending from the second finger grip 118 positioned substantially parallel to the first tine 110. Further, the inner surface of the first tine 110 and the second tine 120 curved to form a first opening 122 adjacent to the pivot point 106 for storing of articles (not shown in FIG. 1). The first finger grip 108 and the second finger grip 118 are explained in detail in conjunction with FIG. 6 of the present invention. The first opening 122 is explained in detail in conjunction with FIG. 6 and FIG. 7 of the present invention.

The second shear 104 includes a second cutting edge 124 extending from the second tine 120 having a second curved inner surface front end 126. The first curved inner surface front end 114 and the second curved inner surface front end 126 forms a second opening 127 for holding substantially smaller articles, and a second gripping tip 128 attached to the second cutting edge 124 for gripping of articles (not shown in FIG. 1) against the first gripping tip 116. The second opening 127 is explained in detail in conjunction with FIG. 8 of the present invention.

Further, the multi-purpose tool 100 includes ratchets 109 extending from each finger grip i.e. the first finger grip 108 and the second finger grip 118. The first shear 102 and the second shear 104 are adapted for extending around the article in a firm grip by engagements of the ratchets 109 in order to clamp the article between the first shear 102 and the second shear 104. The ratchets 109 are shown and explained in detail in conjunction with FIG. 2 of the present invention.

In another preferred embodiment of the present invention, the multi-purpose tool 100 further includes a ruler bar 130 on the first cutting edge 112 to measure the cutting area of the article. Further, the multi-purpose tool 100 includes a carabineer 132 configured in between at least one of the first tine 110 and the first finger grip 108 to secure the article.

In another preferred embodiment of the present invention, the multi-purpose tool 100 includes a light source 134 protruding from the outer surface of the first finger grip 108 and a power source 136 configured in between the first tine 110 and the first finger grip 108 to power the light source 134. In a preferred embodiment, the light source 134 is a LED and the power source 136 is a battery.

Figure 2:
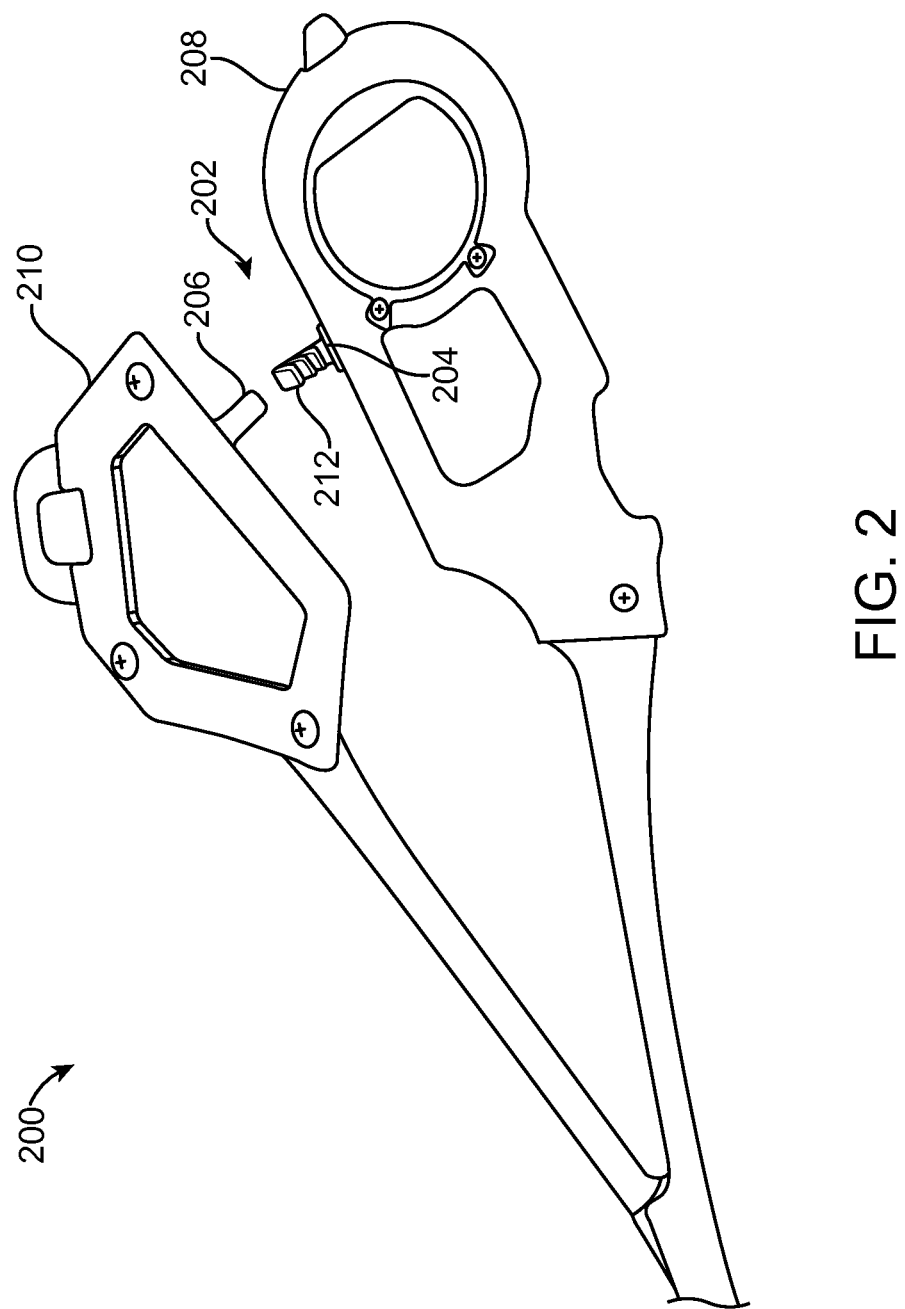
FIG. 2 illustrates another perspective view of a multi-purpose tool showing ratchet in accordance with another preferred embodiment of the present invention.

FIG. 2 illustrates a perspective view of a multi-purpose tool 200 showing ratchets 202 such as a first ratchet 204 and a second ratchet 206 extending from the first finger grip 208 and the second finger grip 210, respectively in accordance with another preferred embodiment of the present invention.

Further, both the ratchets 202 include plurality of ratchet teeth 212 for engaging with each other. The ratchet teeth 212 are grooves that fit in one another on application of force to incrementally increase the clamping pressure on the article by the user to bring the first ratchet 204 and the second ratchet 206 close to each other.

In a preferred embodiment of the present invention, the first ratchet 204 and the second ratchet 206 are used to clamp IV tubes and thus facilitating users to remove and or tighten the IV hubs and ends of intravenous tubing. Further, the first ratchet 204 and the second ratchet 206 may be used for removal and tightening of other joints in the intravenous tubing.

Figure 3:
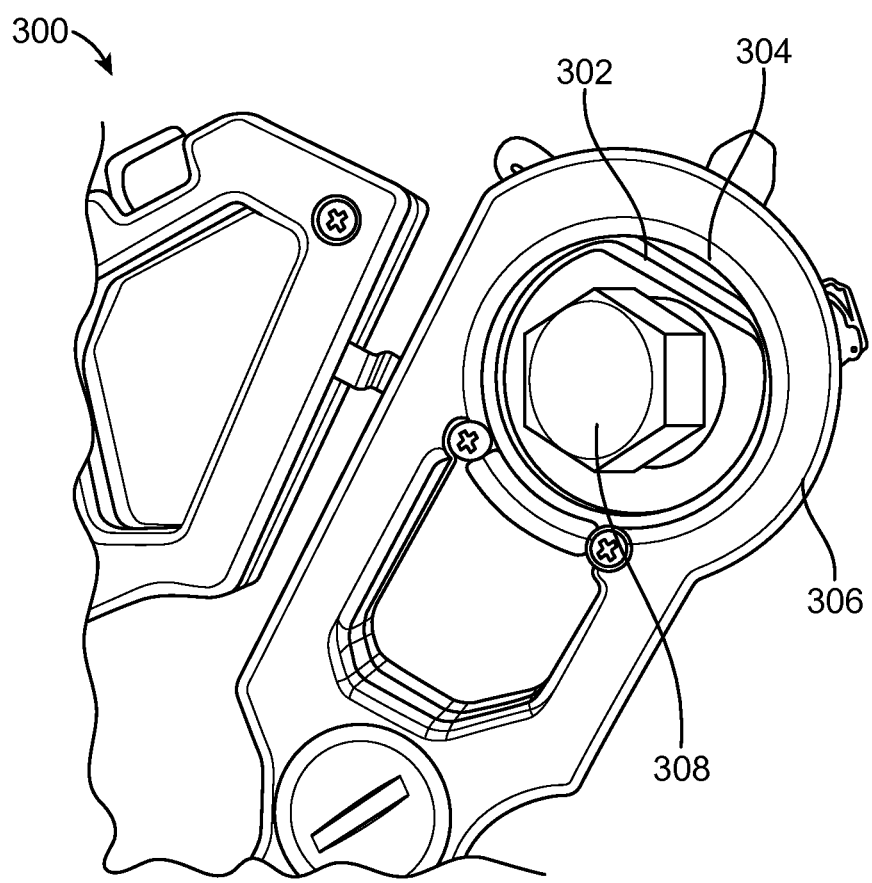
FIG. 3 illustrates another perspective view of the multi-purpose tool showing a bottle opener configured in the inner surface of at least one of the finger grips in accordance with another preferred embodiment of the present invention.

FIG. 3 illustrates another perspective view of the multi-purpose tool 300 showing a bottle opener 302 configured in the inner surface 304 on the first finger grip 306 in accordance with another preferred embodiment of the present invention. The bottle opener 302 is configured for opening of the bottle cap 308.

The bottle opener 302 is configured along the circumference of the first finger grip 306. Preferably, the bottle opener 302 is made of stainless steel for opening of bottle caps. It would be apparent to those skilled in the art that various uses of the bottle opener 302 may be envisioned without deviating from the scope of the present invention.

Figure 4:
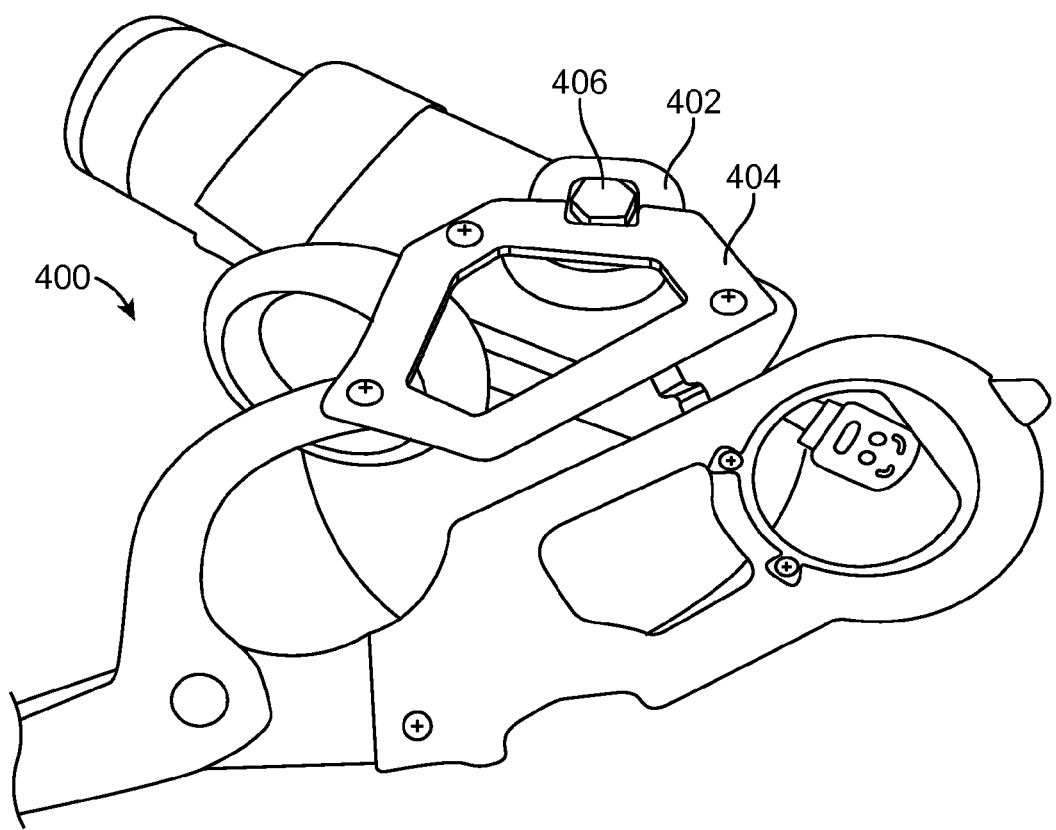
FIG. 4 illustrates another perspective view of the multi-purpose tool showing oxygen key attached to at least one of the finger grips in accordance with another preferred embodiment of the present invention.

FIG. 4 illustrates another perspective view of the multi-purpose tool 400 showing oxygen key 402 attached to the second finger grip 404 for operating an oxygen tank valve 406 in accordance with another preferred embodiment of the present invention. The oxygen key 402 is an elongated rectangular block preferably of stainless steel/aluminum configured to match the shape and size of the oxygen tank valve 406.

The oxygen key 402 either turns on or off the oxygen tank valve 406. It would be apparent to those skilled in the art that various uses of the oxygen key 402 may be envisioned without deviating from the scope of the present invention.

Figure 5:
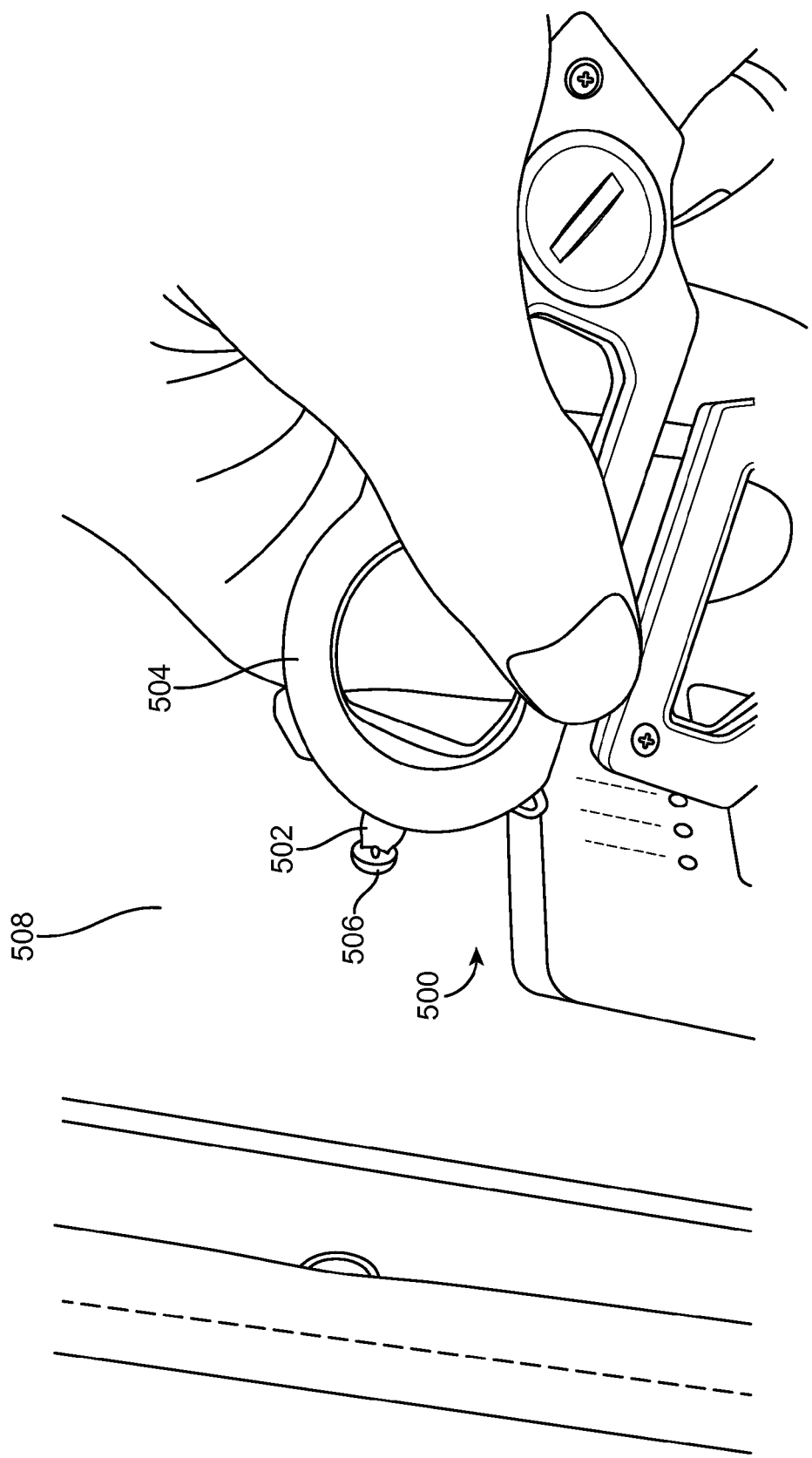
FIG. 5 illustrates another perspective view of the multi-purpose tool showing screw driver tip configured on at least one of the finger grips in accordance with another preferred embodiment of the present invention.

FIG. 5 illustrates another perspective view of the multi-purpose tool 500 showing screw driver tip 502 configured on the first finger grip 504 for opening screw 506 of a box 508 in accordance with another preferred embodiment of the present invention. The screw driver tip 502 is an elongated body extending away from the first finger grip 504.

In a preferred embodiment of the present invention, the screw driver tip 502 opens flathead and philips screw size no. 2. Further, in another preferred embodiment of the present invention, the screw driver tip 502 may further be used for splitting pills while they remain in packaging, scraping residue off articles and opening of cardboard boxes. It would be apparent to those skilled in the art that various uses of screw driver tip 502 may be envisioned without deviating from the scope of the present invention.

Figure 6:
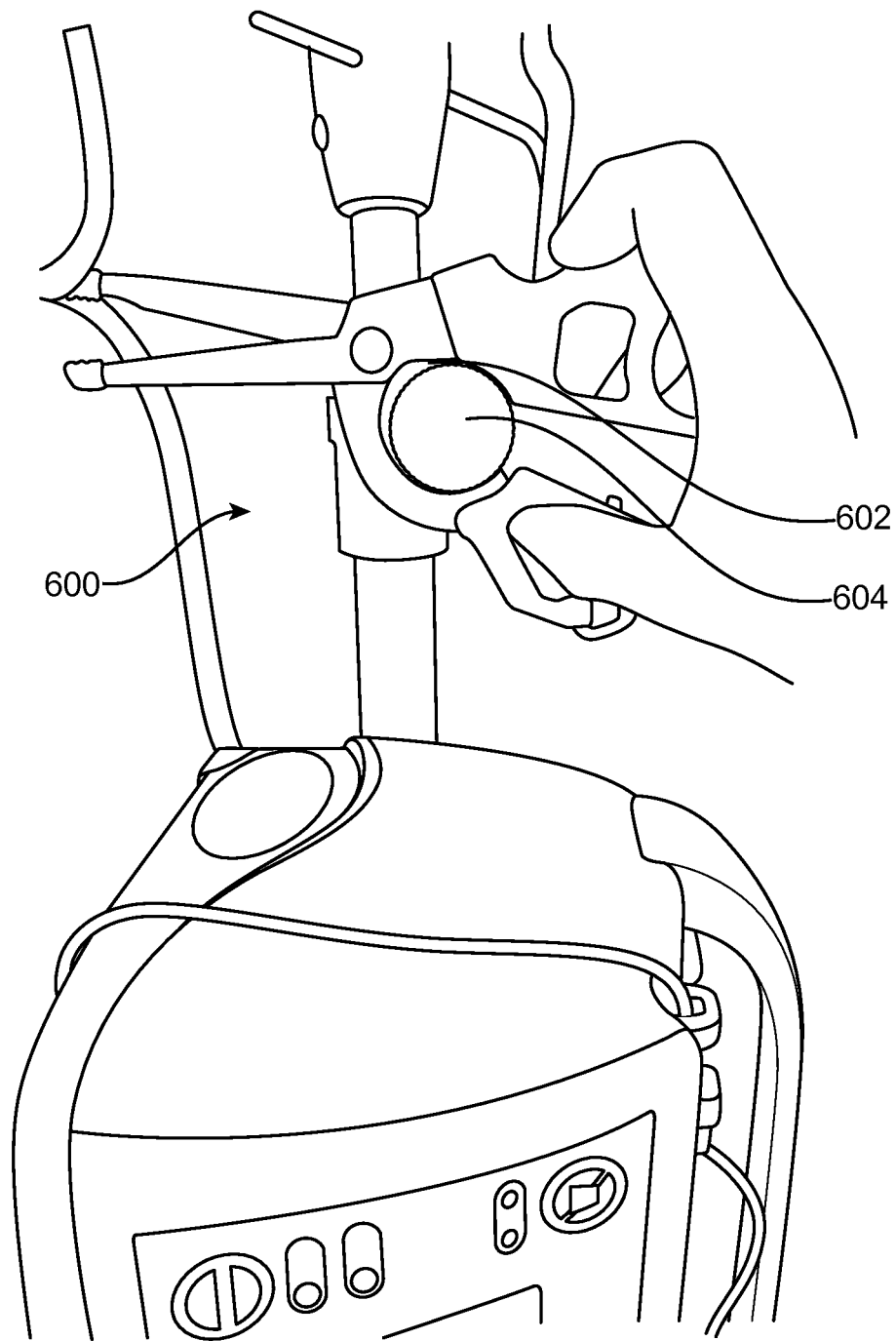
FIG. 6 illustrates another perspective view of the multi-purpose tool showing the first opening for tightening and opening of medical equipment knobs in accordance with another preferred embodiment of the present invention.

FIG. 6 illustrates another perspective view of the multi-purpose tool 600 showing first opening 602 for grasping of knob 604 in accordance with another preferred embodiment of the present invention. With reference to FIG. 1, the first opening 602 has ribbed inner surface to fit around the knob 604 and further facilitates in screwing or unscrewing of the knob 604.

Figure 7:
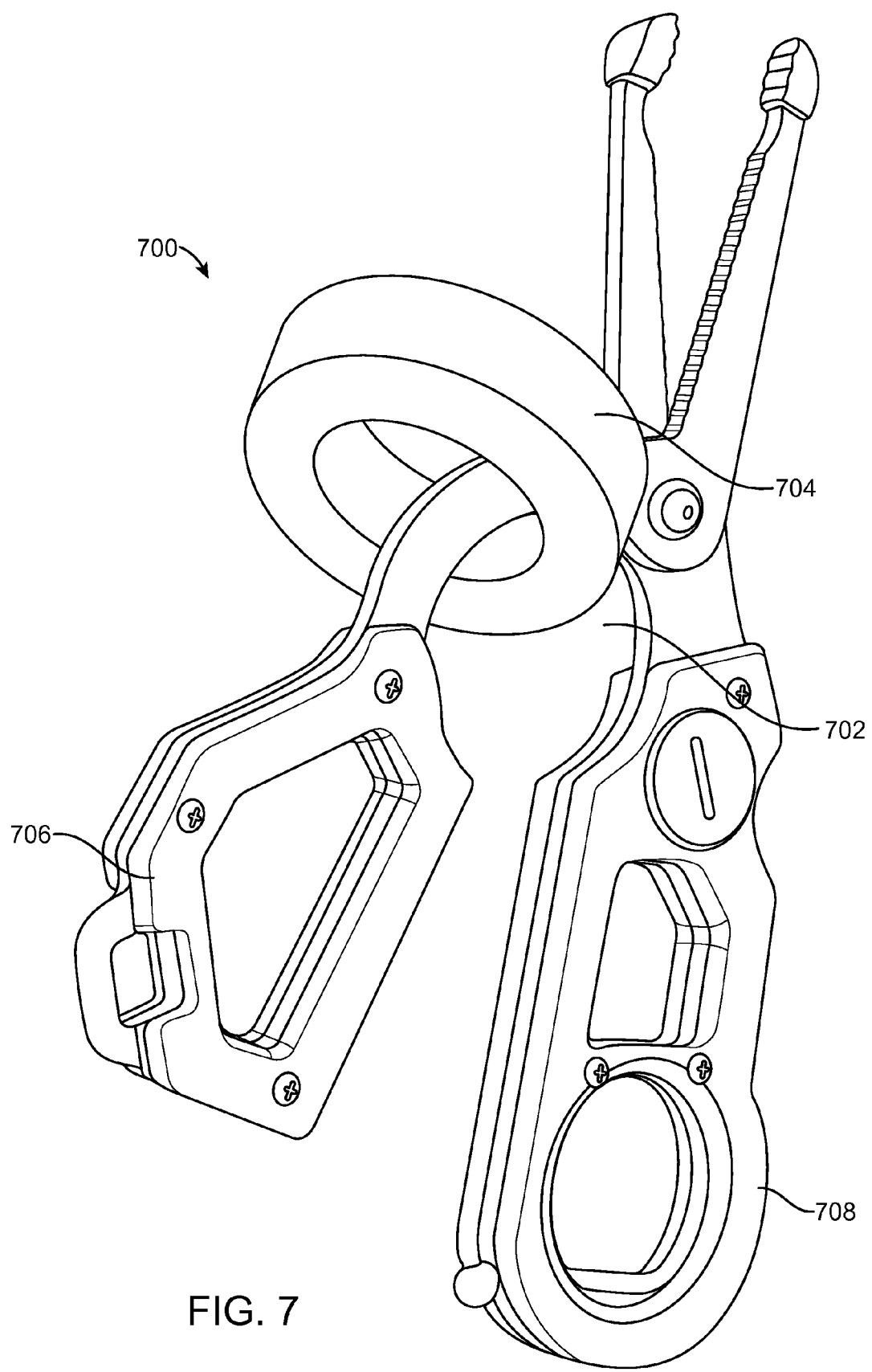
FIG. 7 illustrates another perspective view of the multi-purpose tool showing the first opening for storing of articles in accordance with another preferred embodiment of the present invention.

FIG. 7 illustrates another perspective view of the multi-purpose tool 700 showing the first opening 702 for storing of a tape 704 in accordance with another preferred embodiment of the present invention. The first opening 702 allows the storage of tape 704 when the first finger grip 706 is far from the second finger grip 708. Further, the tape 704 moves over the first finger grip 706 to store in the first opening 702.

Figure 8:
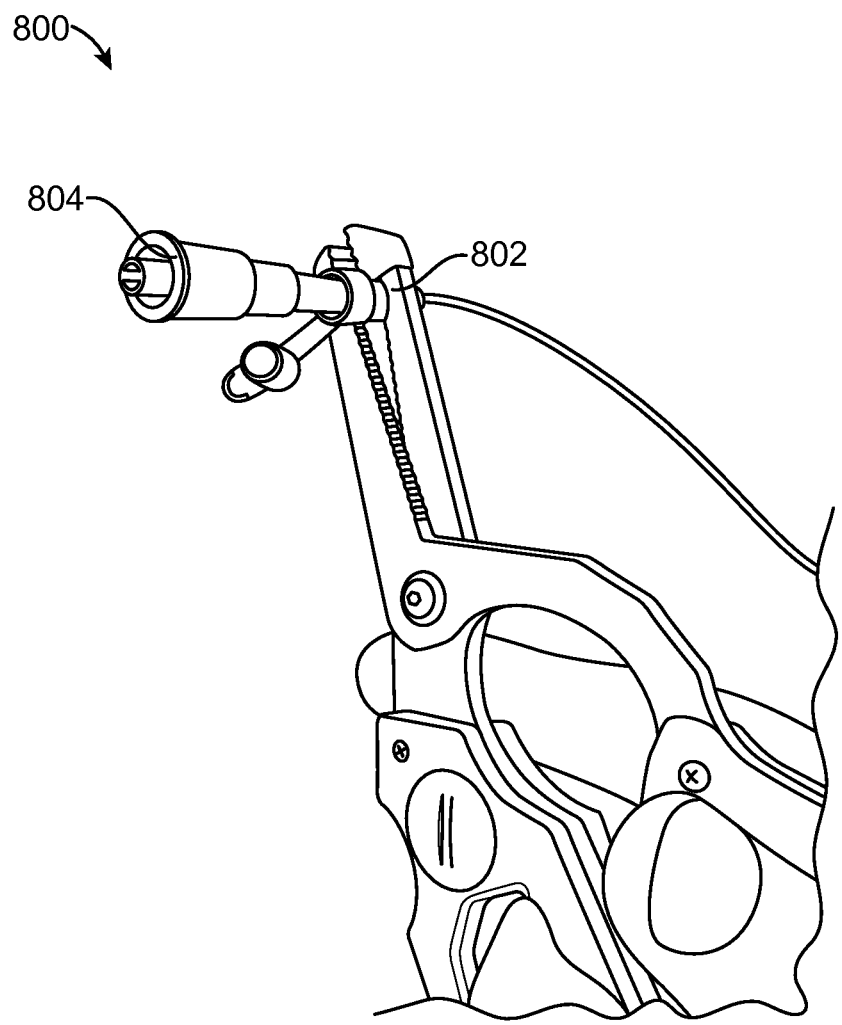
FIG. 8 illustrates another perspective view of the multi-purpose tool showing the second opening for storing of a IV/Medical tube in accordance with another preferred embodiment of the present invention.

FIG. 8 illustrates another perspective view of the multi-purpose tool 800 showing the second opening 802 for holding of a IV/Medical hub 804 in accordance with another preferred embodiment of the present invention. With reference to FIG. 1, the second opening 802 allows the user to grab the medical tube 804 by bringing the finger grips closer. In another preferred embodiment of the present invention, the ratchets may further be used to clamp the IV tube, so that it is easier to remove the IV/medical hub 804 without spillage of fluids.

The present invention offers various advantages especially in the medical field. The present invention offers frontline medical clinicians to treat patients in a more efficient way. The present tool saves time and effort of the user and further allowing increased focus on the patient's clinical status. The present tool reduces hunting and gathering of individual equipments during critical medical needs of the patient.

The many features and advantages of the invention are apparent from the above description. It is apparent from the foregoing that a new and improved multi-purpose tool has been provided. The invention is quite simple and can be used on different surfaces. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

The invention claimed is:

1. A multi-purpose tool operated by a user for storing, opening, cutting, clamping and holding of articles comprising:
   a first shear comprising:
      a first finger grip for receiving at least one finger of a user;
      a first tine extending from the first finger grip;
      a first cutting edge extending from the first tine having a first curved inner surface front end;
      a first gripping tip attached to the front end of the first cutting edge; and
   a second shear movably coupled to the first shear at a pivot point comprising:
      a second finger grip for receiving at least one finger of the user;
      a second tine extending from the second finger grip positioned substantially parallel to the first tine, wherein the inner surface of the first tine and the second tine curved to form a first opening adjacent to the pivot point for opening of articles;
      a second cutting edge extending from the second tine having a second curved inner surface front end, wherein the first curved inner surface front end and the second curved inner surface forms a second opening for holding substantially smaller articles; and
      a second gripping tip attached to the second cutting edge for gripping of articles against the first gripping tip; and
   a ratchet extending from each finger grip, each ratchet having a plurality of ratchet teeth defined therein, the ratchets extending towards each other;
   wherein the first shear and the second shear are adapted for extending around the article in a firm grip by engagement of the ratchets in order to clamp the article between the first shear and the second shear.

2. The multi-purpose tool according to claim 1 wherein the first opening stores at least one article when the first finger grip is far from the second finger grip, further the article moves over at least one of the finger grips to store in the first opening.

3. The multi-purpose tool according to claim 1 further comprising a ruler bar on at least one of the first cutting edge; and the second cutting edge.

4. The multi-purpose tool according to claim 1 further comprising an oxygen key attached to at least one of the finger grips.

5. The multi-purpose tool according to claim 1 further comprising a bottle opener configured in the inner surface of at least one of the finger grips.

6. The multi-purpose tool according to claim 1 further comprising a screw driver tip configured on the outer surface of at least one of the finger grips.

7. The multi-purpose tool according to claim 1 further comprising:
   a light source protruding from the outer surface of at least one of the finger grips; and
   a power source configured in between at least one of the tine and at least one of the respective finger grips to power the light source.

8. The multi-purpose tool according to claim 1 further comprising a carabineer configured in between at least one of the tines and at least one of the respective finger grips to secure articles.

9. The multi-purpose tool according to claim 1 wherein the user depresses the finger grips to clamp a part of the article in between the ratchets.

* * * * *